(12) United States Patent
Fiset

(10) Patent No.: US 7,476,888 B2
(45) Date of Patent: *Jan. 13, 2009

(54) SKIN TANNING AND LIGHT THERAPY INCORPORATING LIGHT EMITTING DIODES

(76) Inventor: Peter D. Fiset, 5 Upper Loudon Rd., Loudonville, NY (US) 12211

( * ) Notice: Subject to any disclaimer, the term of this patent is extended or adjusted under 35 U.S.C. 154(b) by 0 days.

This patent is subject to a terminal disclaimer.

(21) Appl. No.: 11/732,667

(22) Filed: Apr. 4, 2007

(65) Prior Publication Data

US 2008/0035864 A1 Feb. 14, 2008

Related U.S. Application Data

(63) Continuation of application No. 11/044,614, filed on Jan. 27, 2005, now abandoned, which is a continuation of application No. 10/714,824, filed on Nov. 17, 2003, now Pat. No. 6,861,658.

(60) Provisional application No. 60/473,237, filed on May 24, 2003.

(51) Int. Cl.
*A61N 5/00* (2006.01)
*A61N 5/08* (2006.01)

(52) U.S. Cl. ............... 250/504 R; 250/494.1; 250/493.1; 250/461.1; 250/365; 257/88; 257/98; 607/88; 607/91

(58) Field of Classification Search ............. 250/504 R, 250/494.1, 493.1, 461.1, 365; 257/88, 98; 607/88, 91
See application file for complete search history.

(56) References Cited

U.S. PATENT DOCUMENTS

| | | | | |
|---|---|---|---|---|
| 6,828,576 | B2* | 12/2004 | Spivak | 250/504 R |
| 6,861,658 | B2* | 3/2005 | Fiset | 250/504 R |
| 7,229,467 | B2* | 6/2007 | Spivak | 607/88 |
| 2007/0208395 | A1* | 9/2007 | Leclerc et al. | 607/86 |

* cited by examiner

*Primary Examiner*—Nikita Wells
(74) *Attorney, Agent, or Firm*—Elmore Patent Law Group, PC; Carolyn S. Elmore, Esq; Darlene A. Vanstone, Esq

(57) ABSTRACT

The invention relates to a skin tanning chamber, the improvement comprising at least one light emitting diode emitting a UVA light, such as a UVA LED that emits essentially only UVA. Additionally, multiple LEDs of varying types with various characteristic wavelengths are controlled independently to produce an arbitrary light pattern in an arbitrary sequence over time. The chamber can be rigid or flexible. It can be a bed, booth or incorporated into a flexible form, such as a garment or cloth. In one embodiment, the chamber further comprises at least one LED emitting a UVC light, whereby the UVC light sanitizes the chamber surface. Preferably the LED emitting the UVA light is under independent control from the LED emitting UVC light.

19 Claims, 3 Drawing Sheets

SKIN TANNING AND LIGHT THERAPY INCORPORATING LIGHT EMITTING DIODES

RELATED APPLICATIONS

This application is a continuation of U.S. application Ser. No. 11/044,614, filed Jan. 27, 2005, now abandoned which is a continuation of U.S. application Ser. No. 10/714,824, filed Nov. 17, 2003, now U.S. Pat. No. 6,861,658 which claims the benefit of U.S. Provisional Application No. 60/473,237, filed on May 24, 2003. The entire teachings of the above applications are incorporated herein by reference.

BACKGROUND OF THE INVENTION

The most common method of skin tanning involves the process of exposing skin to ultra-violet light. Health research has shown that both the condition of under-exposure to ultra-violet light and the condition of over-exposure to ultra-violet light causes a variety of health problems. Health research has also shown that specific ranges of wavelengths of ultra-violet light are responsible for producing health benefits. Moderate exposure to specific wavelengths of ultra-violet light produces the greatest benefits with the least amount of health risk. Certain methods and devices are useful at controlling the quantity and quality of ultra-violet light exposure in the effort to produce the greatest health benefits with the least amount of health risks. Ultra-violet light quality depends primarily on the ranges of wavelength of ultra-violet light; where the highest ultra-violet light quality is the ultra-violet light that produces the greatest net health benefits.

The sun is a primary source of ultra-violet light for tanning. The quantity of light exposure to the sun is simple to control. The quality of ultra-violet light exposure by the sun is not simple to control. Lamps that provide alternative sources of ultra-violet light allow for tanning services that do not rely on the sun. These tanning services are available and are administered in a controlled environment such as in personal care service salons. The industry providing controlled exposure to artificial ultra-violet light is generally referred to as the "indoor-tanning" industry. Indoor-tanning does not implement systems that are directly dependent on the sun as the source of ultra-violet radiation. The quality of the indoor-tanning ultra-violet light has become important in differentiating services available within the same indoor-tanning salon and between competing tanning salons.

Light with wavelengths in the ultra-violet range is often referred to as UV light or UV. UVA, UVB and UVC describe three separate non-overlapping but adjacent ranges of light fully encompassing the UV light range. The range of light referred to as UVA generally has the longest set of wavelengths within the UV range and includes wavelengths between 290 and 400. UVA-1, as that termed is used herein, is between 340 and 400; UVA-2 is between 315 and 340; and UVA-3 is between 290 and 315. The range of light referred to as UVC generally has the shortest set of wavelengths within the UV range and includes wavelengths between 160 and 260. The range of light referred to as UVB includes wavelengths between 260 and 290.

The use of the terms UVA, UVB and UVC allow the various properties of UV light to be categorized in general ways. UVA has the best capability of tanning skin. UVB does not produce a tan in the third layer of skin. UVC light does not produce a tan but can sterilize some biological agents such as certain bacteria. Under certain conditions UVB will tan the second layer of skin. The second layer of skin when tanned with UVB has a shedding period of 5 to 8 days. Skin tanned with UVA only has the third layer of skin tanned which results in a normal shedding cycle of 28 days.

A light therapy is a method of applying a specific set of wavelengths of electromagnetic radiation in specific states and under specific conditions to produce a change in a bodily function. Tanning is a light therapy whereby the biological change is the production of melanin within the cells of the skin. Indoor-tanning is a light therapy utilizing the exposure of moderate amounts of UV over a reasonable amount of time to skin from UV sources other than the sun.

Under normal conditions the outer layer of skin, also known as the first layer, is composed of dead cells. Normally, dead cells will not produce melanin upon exposure to moderate amounts of UV. The layer under the first layer of skin is referred to as the second layer of skin, and is composed of active cells that may be functioning in some biological manner and will produce melanin upon exposure to UVB light. UVB skin tanning has, what some tanners consider, an additional negative effect, UVB tanning will thicken the second layer of skin and as a result increases the visibility of skin lines and wrinkles. UVB tanning creates a shedding cycle of 5 to 7 days which is undesirable when a UVA tan has a shedding cycle of 28 days. When UVB is combined with UVA the shedding cycle of the UVA tanned layer is accelerated since the second layer is shed more quickly and the third layer becomes the second layer as a result and is shed within another 5 to 7 days.

Under normal conditions the layer of skin that will produce melanin (melanogenesis) when exposed to UVA-3 or UVB light is referred to as the third layer of skin and more specifically the melanocytes within the skin. The Vitamin-D production is believed to be caused by exposure to UVA-3 or UVB light. However, UVB light can also degrade Vitamin-D. Since UVA-3 does not degrade Vitamin-D, UVA-3 is preferred over UVB for Vitamin-D production and melanogenesis. The selective elimination of UVB and selective production of UVA-1, UVA-2 and UVA-3 can be a benefit of the present invention. Melanogenesis is important for tanners who desire a darker tan than that which is obtained from UVA-1 or UVA-2 exposure alone. UVA-1 and UVA-2 converts melanin into the dark pigment melatonin. The Tanning Industry Association promotes a skin-type classification based on the amount of melanin present in the skin before additional melanin has been created by melanogenesis. These types include type I (little), II (low), III (moderate), IV (high) and V (black). In exceptional conditions such as albinism, the third layer of skin is not capable of producing melanin. For the purposes of this application, albino skin is considered an exception to the norm and will not be referred to as a third layer of skin but as an albino third layer of skin.

It is common knowledge that all wavelengths of UV over long exposure periods damage the skin in various ways. Therefore, it is desirable to limit the exposure of UV radiation to skin. Alternatively, some UV exposure is generally considered necessary in order to maintain good health in other bodily functions, such as the generation of vitamin-D. Vitamin-D is useful in the absorption of calcium in the body. Therefore, it has been recommended by various health organizations studying the phenomena that moderate exposure to UV light has a net health benefit, whereas over-exposure or under-exposure of UV results in a net health deficit. The art of indoor-tanning to remain useful should provide for ever increasing controllability of the application of the light therapy. As a light therapy tanning should be applied with specific goals and procedures to maximize the benefits of the therapy.

For people desiring a tan, the main benefits of UV exposure is the production of tanned skin. Tanners enjoy positive psychological and perceived positive social benefits resulting from having tanned skin. In order to limit the total amount of UV radiation tanners are exposed to while maintaining a tan, it is desirable to reduce as much as possible the exposure to UV light outside the UVA wavelength range. UVB and UVC wavelength ranges of radiation are by definition not capable of tanning skin with a 28 day shedding cycle and therefore reasonable efforts should be made to eliminate UVB and UVC from the source of light tanners are exposed to.

Indoor-tanning methods generate UV light from converting electrical energy to light within devices such as UV fluorescent bulbs and high pressure quartz metal-halide bulbs, which are two specific types of light bulb technologies. UV light bulbs currently in use have properties of high voltage, high temperature, and low electrical energy to UV conversion efficiencies of approximately seventeen percent.

Within the fluorescent light bulb category there are a variety of types that differ mainly in the percentage of UV light produced in the UVA, UVB and UVC wavelength ranges. For tanners concerned with overexposure to UV light the more desirable fluorescent bulbs have a higher percentage of light in the UVA wavelength range. Tanners concerned with overexposure prefer and tend to pay a premium for tanning services that have the least amount of UVB and UVC.

Depending on weather conditions, typically 88% of the UV radiation from the sun is UVA, in this case an artificial source with more than 88% of the UV radiation is UVA is considered a less harmful tanning method than sun-tanning. Common fluorescent tanning bulbs and associated services have UV composed between 92.0%. UVA to 97.5% UVA. Currently, high pressure quartz metal-halide bulbs have in general 98.5% UVA and are considered to be the least harmful artificial tanning bulbs currently used in indoor-tanning salons.

SUMMARY OF THE INVENTION

The invention relates to a skin tanning chamber, the improvement comprising at least one light emitting diode emitting a UVA light, such as a UVA LED that emits essentially only UVA. Additionally, multiple LEDs of varying types with various characteristic wavelengths are controlled independently to produce an arbitrary light pattern in an arbitrary sequence over time. The chamber can be rigid or flexible. It can be a bed, booth or incorporated into a flexible form, such as a garment or cloth. In one embodiment, the chamber further comprises at least one LED emitting a UVC light, whereby the UVC light sanitizes the chamber surface. Preferably the LED emitting the UVA light is under independent control from the LED emitting UVC light.

The skin tanning chamber preferably comprises a plurality of LEDs emitting UVA light, optionally, further comprising a means for controlling the electric current to each LED to maintain a calibration for a consistent radiant flux over the life time of each LED; a means for controlling the LEDs to allow radiation to selected portions of the skin; a means for controlling the period of exposure; a means for selecting and controlling wavelengths emitted, a means to vary radiant flux and wavelengths according to a program responsive to combinations of feedforward and feedback sensors, and a means for storing records of use.

In another embodiment, the LED is incorporated into a form which is adapted to fit into a standard fluorescent bulb fixture and can have an internal or an external power converter to permit the use of a UVA LED in a conventional fluorescent tube-based device with cooling means, air flow means and temperature control means.

The skin tanning chamber preferably is configured to permit ventilation of the LEDs, such as by a fan which blows a gas, such as air, longitudinally or laterally across the LEDs. In one embodiment, the LEDs are disposed within a transparent or translucent, preferably acrylic, tube characterized by one or more perforations which provide for air flow out of the tube. The tube can be characterized by a closed end and an open end, wherein the air is directed through the open end and out the perforations. The density of perforations on the distal end of the tube, with respect to the open end, can be greater than the density of perforations on the proximal end and/or they can be larger than the perforations on the proximal end. This results in improved performance and longer life for the LEDs.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
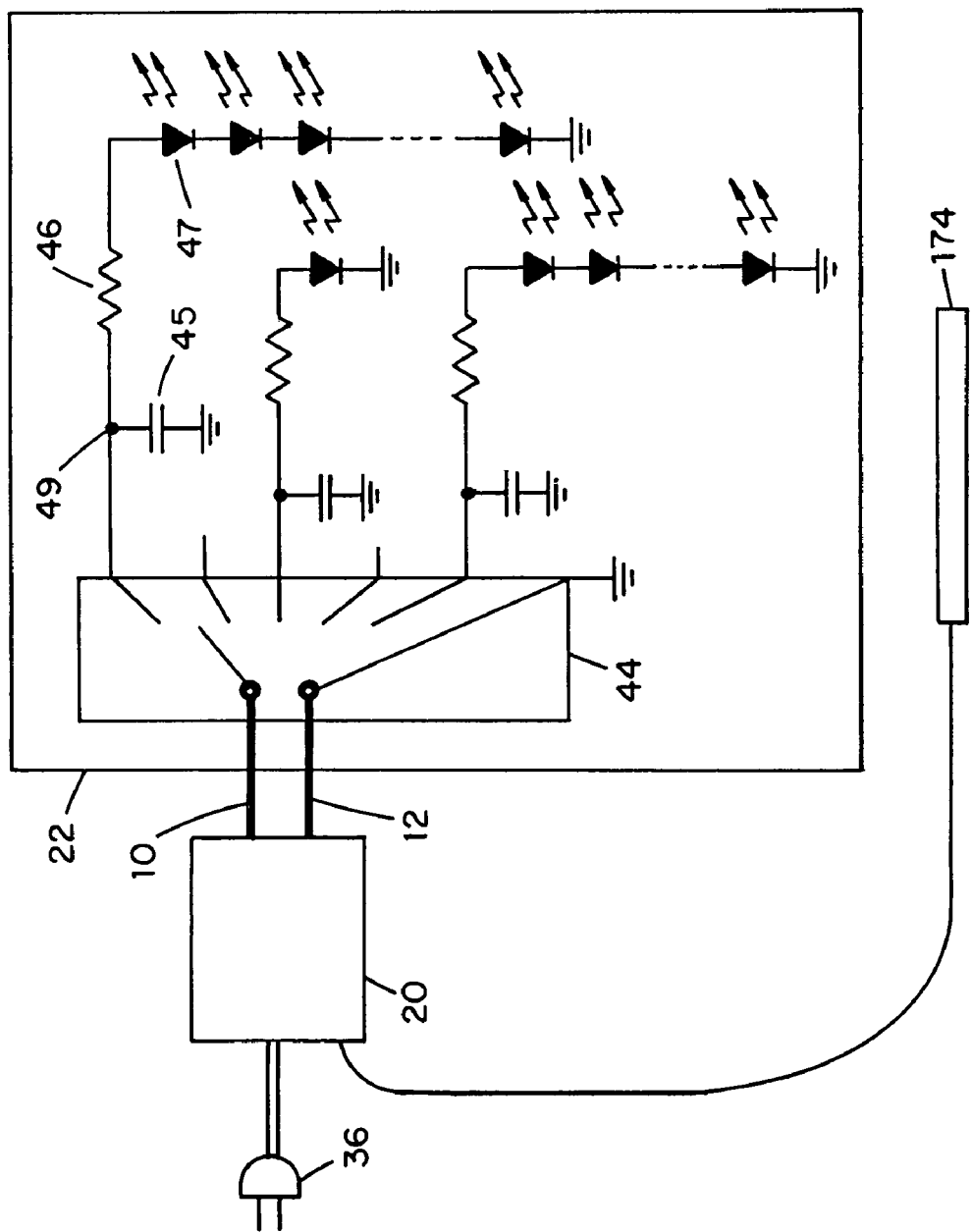
FIG. 1 shows an electrical schematic diagram for powering the LEDs in the series connected LEDs (47) in the low voltage LED array (22) and metallic pins (10, 12) and external LED compatible power supply (20) responding to control from optional external light output feedback sensor (174) and house power connector (36). This embodiment utilizes a resistor (46) to limit the current to the series connected LEDs (47). The series connected LEDs (47) have multiple LEDs or a single LED depending on the voltage supplied and number LEDs per controlled power lines (49). If the design goals of further embodiments of the present invention requires a controllable power line for each LED then a single LED in the series connected LEDs (47) and LED (5) are identical. There is a tradeoff between providing control to each LED and the cost associated with the control circuits. Additionally, there is a tradeoff between cost of power supply and the failure of a single LED in an open failure mode to block the delivery of current to multiple LEDs in the series connected LEDs (47). LED compatible power supplies (20) designed for supplying current to individual LEDs is more expensive because the voltage conversion is wider and the current output is higher. The total current output from LED compatible power supply (20) is reduced by a factor calculated as the number of power lines (49) divided by the total number of LEDs in the further embodiment of invention (22). Therefore, depending upon the application and allowable failure modes, LEDs may have an arbitrary number of LEDs in series depending on the trade-off and application requirements. Also shown is a variable power supply which charges capacitors (45) in a selective manner.

The present invention incorporates the use of light emitting diodes, commonly referred to as LEDs, into an indoor-tanning device that optionally includes other sources of therapeutic electromagnetic radiation. UVA LEDs are preferred. Particularly preferred UVA LEDs include those that emit at least about 90% UVA wavelengths, preferably at least about 95% or more UVA wavelengths. In one embodiment, the LED emits essentially only (e.g., at least about 99.99%) UVA. This high percentage of UVA light output is an improvement over previous lamp technologies previously available in indoor-tanning salons. The various LED manufacturers of the preferred LEDs are Cree Inc. (USA), Nichia (Japan), Toyoda Gosei (Japan), Crystal IS (USA—Aluminum Nitride AlN substrate) with Palo Alto Research Center (USA).

For providing general purpose light therapy it is desirable to include LEDs that have wavelengths in addition to UVA to provide for services other than or in addition to tanning. Therefore in light therapy other than tanning a mix of various wavelength LEDs may be incorporated in combinations that suit a particular therapy requirement. A light therapy device composed of UVA LEDs and other LEDs and other types of light bulbs is desirable to provide a variety of desired therapeutic effects. When the desired effect is tanning skin then a portion of the LEDs are of the UVA LED variety. In general, UVA LEDs are used in combination with other light sources to produce a combination light therapy in a selectable and controllable manner. Light therapy devices with multiple and varied types of lamps include selectable power supplies that control how and when the various lamps are powered. Indoor-tanning devices with selectively controllable UVA LEDs have the advantage of providing selectable tanning areas and reduced power when tanning is not required at various points within the tanning chamber.

There are many advantages of LEDs over light bulbs. LEDs are more efficient at converting electrical energy into directed light than many other UV light bulb types. LEDs do not require surfaces operating at high temperatures and can be safer. LEDs do not require high voltages or high currents to operate and, for this reason, LEDs are safer and require less structure to protect the people in proximity to the light source. Additionally, LEDs can be smaller than light bulbs. As discrete components LEDs may be fabricated as arrays in a wide variety of shapes and form factors, including a fluorescent bulb form factor, an industry standard light bulb, or an industry standard spot light bulb.

In a fluorescent bulb form factor the UVA LED arrays can contain an internal power conversion or external power conversion (or a combination of internal and external power conversion) and directly replace a UV fluorescent bulb in currently installed tanning devices currently made for indoor-tanning devices. Current indoor-tanning devices for the prone body position are commonly referred to as tanning beds. Current indoor-tanning devices for upright body positions are commonly referred to as tanning booths. Collectively, tanning booths and tanning beds are referred to as tanning chambers.

In a further embodiment of the invention, UVA LEDs are incorporated into articles of clothing, and into cloth, and into flexible forms, and into rigid forms that allow for home tanning systems and for personal tanning systems such as tanning jackets, tanning pants, tanning suits, tanning bags or sacs, tanning blankets and tanning rooms.

Personal tanning systems can be shared by different people at different times. If a personal tanning system is shared, it is desirable to have a set of removable UVA-translucent garment or liner capable of being washed. A personal tanning system that is cleaned in an efficient manner between uses is desirable. A personal tanning system with the ability to be cleaned is desirable whether shared or un-shared.

UV light has surface sterilization effects and therefore a personal tanning system will to some degree be self-cleaning with regard to certain undesirable bacteria such as mold and mildew. Additionally, UVB and UVC light sources may be incorporated into a personal tanning device to produce a higher degree of sterilization when operated in a special cleaning mode without the presence of tanners.

In ideal conditions, UV LED semiconductor chips have a lifetime on the order of 100,000 hours. Encapsulated LEDs have an epoxy or plastic encapsulation. The encapsulated UV LEDs have an effective lifetime of 10,000 hours due to degradation of the encapsulation material from UV exposure. The chips within the encapsulation continue to operate past the 10,000 hours but the UV degraded encapsulation material does not allow as much UV light to escape. In order to maintain a calibrated constant total radiant flux per tanning session over the life of the encapsulated UV LED based tanning device, then either, the corrective action of increasing the electric current supplied to the LEDs, or the corrective action of increasing the total number of powered. LEDs in the tanning device, or a combination of the corrective actions must be taken as the encapsulation material degrades. The wavelength of the UVA does not change significantly over the life of a UVA LED.

When used in 5 to 20 minute power cycles common in tanning chambers, fluorescent light bulbs begin to noticeably degrade within 100 hours of use and have a total lifetime on the order of 1000 hours or less, and are very often replaced after 400 total hours of operation creating significant maintenance expenses. Therefore, there is a greatly reduced amount of maintenance required with the LED based tanning systems as opposed to fluorescent bulb tanning systems. The UVA LED has a consistent wavelength over the life of the LED, whereas the wavelength varies for fluorescent bulbs over the life of the fluorescent bulb. The average wavelength of the fluorescent bulb in the UVA range decreases and drifts into the UVB range which is considered by some tanners as a negative effect over the life of the fluorescent bulb. Independent of UVA LED mounting method, whether encapsulated in UV sensitive material (epoxy resin) or encapsulated in UV insensitive materials (metal or plastic housing with quartz lens), the UVA LEDs have a longer useful life than fluorescent bulbs.

As previously stated, UVA LEDs may be used in combination with other UV producing light sources. LEDs incorporated into light therapy devices, including tanning devices, are not limited to the UVA type only. Other wavelengths LEDs are incorporated into the device in order to provide other types of light therapy. In addition to providing additional light therapy effects, other wavelength LEDs may provide visible light in an otherwise dark chamber.

In any UV light exposure application it is recommended for people being exposed to use UV opaque protective eye-wear, and it is recommended for people being exposed to shut the eyelids as much as possible in order to minimize exposure of the retina to UV. It is important to maintain strict observation of the requirement for UV opaque protective eye-wear during operation of tanning equipment. Therefore, in one embodiment, special control circuits can be incorporated to prevent powering the UV light sources when UV opaque UV opaque protective eye-wear in absent. In addition, training in use of tanning equipment is highly recommended.

This present invention is a reliable tanning device incorporating combinations of sensors and communication equipment into the tanning device to determine if the tanner has UV opaque protective eye-wear present and worn correctly before allowing the tanning system to start emitting UV radiation. This reliable personal tanning device incorporates special safety features that identify people and do not allow for over-exposure of any user to UV light over a given time frame. This reliable personal tanning device interfaces to a computer terminal with associated software logic and with associated input and output control ports, to provide information such as length of tan for a each unique user and to provide historical records of user specific tanning activities and accounting details.

In one embodiment, the LED device is contained in a tube, such as an acrylic tube, in the form factor of an industry standard fluorescent bulb with an internal power converter, an optional internal cooling system, and an optional temperature sensor. In yet another embodiment, the form is equipped with an internal light output feedback sensor to control the power to the cooling system or other fan. Alternatively, an external LED compatible power supply in the form factor for a high voltage fluorescent bulb ballast power supply can be used with the LED device in the fluorescent bulb form factor with house-power volt connector. This form factor allows for direct replacement of industry standard fluorescent power ballast when the industry standard fluorescent bulbs are replaced with LED fluorescent bulb form factors which do not contain internal power converters. The invention, manufactured in a standard fluorescent form factor, allows direct replacement with minimal modification to bulb fixtures already deployed in tanning chambers.

An external LED compatible power supply used with a low voltage LED array can be connected to a house-power connector. A low voltage LED array does not need an active internal high voltage power converter and thus has a lower cooling requirement but can still have an optional fan and optional temperature sensor and temperature controller.

In one embodiment, the device is equipped with optional adjustable rotating electrical connectors, friction plate, and fastener, allowing for setting arbitrary direction of the LEDs and circuit board. The device can also be equipped with a porous end-cap that allows for ventilation, such as passive or active ventilation. The porous end cap permits air flow when used, for example, with a fan. The industry standard electrical connection is composed of metallic pins and insulators, commonly referred to as Bi-Pin, RD2 and lead wires.

Flexible electrical connectors are a preferred embodiment, employing coiled wire but could also be composed of a track and slider connector for maintaining electrical connection while allowing for rotation of the end-cap with respect to the circuit board. The rotating components allows for adjustable directional alignment of light without having to rotate the connector on the fixture. In this embodiment, the LED device can advantageously replace one or more fluorescent bulbs in a typical fluorescent bulb based tanning chamber.

The UVA LED based florescent UV bulb replacement apparatus can come in a number of embodiments. In one embodiment, it incorporates an external heat sink for cooling of the components. The built-in power supply conditions house-power or high voltage or high frequency power into power suitable for driving LED circuits. A typical UVA LED fluorescent replacement lamp is composed of thousands of UVA LEDs arrayed on a single fluorescent form factor circuit board. Heat sinks can be integrated into the UVA LED fluorescent replacement lamp. Combinations of heat sinks and fans can be integrated into said present invention. The form factor of the UVA LED fluorescent replacement lamp is similar to that of the florescent bulbs they replace but are not necessarily identical. UVA LED replacement lamps in a fluorescent bulb form factor may replace multiple fluorescent bulbs with a single set of connectors. The UV LED replacement fluorescent bulb set apparatus with a single or multiple sets of rotating electrical connectors can also be used. Optional modular components can create an arbitrary length of fluorescent bulb replacement utilizing special sockets, linking them end to end. Provisions for two-way control signals to selectively control individual or sub-sets of LEDs within the LED array can be contained within the connectors. Alternatively, the power lines can be modulated with two way time or frequency multiplexed coded signals in such a manner as to provide signal information to and from an LED power controller in proximity to the LEDs for the purpose of selectively controlling power to individuals or sub-sets of the LEDs.

The form can contain an array of a plurality of LEDs on a circuit board. The circuit board and LED array can be on one, two or more sides. The board can be flat, curved, angled (such as an obtuse or acute angle with one or two sides of the angle presented with an array). In yet another embodiment, the circuit board LED array is on one or more sides of a multiple angled circuit board, such as an open or closed angled circuit board. Where the board is curved, the curve can be concave, convex, or curvilinear, open or closed (such as a cylinder) with an array presented on one or both sides. In yet another embodiment, the circuit board can be flat (or other configuration), but the LED leads bent to allow direction orientation of LED, distinct from the board. In yet another embodiment, the circuit board is flexible, permitting bending, folding and/or formation to a desired contour. In yet another embodiment, the circuit board and LED array on all points of a curved three-dimensional circuit board.

The invention can be formed in a foldable LED array with multiple flat circuit boards which can be moved relative to each other. This array can be opened and placed on a surface such as a desk or table and can be folded and stored when not in use. A UV opaque safety shroud with an optional door and proximity safety switch encompassing foldable LED array can also be used.

The array of LEDs and circuit board can be made using a chip on board manufacturing process whereby there is no plastic encapsulation for the LED but another form of hermetic sealed cap made of a material with better UV resistant and UV transmittance properties than industry standard LED encapsulation. Industry standard LED encapsulation is typically UV sensitive and reduces the useful life of a UV LED where the LED encapsulation material degrades under UV light conditions over time and thus has a lower UV transmittance over use. Portions of the hermetic seal cap (25) may be composed of glass or quartz or other UV transparent material. Bonding wire can be used to mount the LED chips onto the circuit board. Chip on board mounting increases the lifetime of the UVA LED device because of the elimination of UV degradable encapsulating material.

UVA LED package can be mounted on the surface of the circuit board. The UVA LED package can optionally contain a focused lens typically found in 5 millimeter and 3 millimeter footprints on a circuit board. The hermetically sealed TO-66 package with UVA LED in a metal package with a UV transparent glass or quartz lens on a circuit board can be used. A glass or quartz lens transparent to UVA is preferred over other UV immune UV transparent material including plastic that is not degraded by UVA light.

In yet another embodiment, various UVA LED fluorescent bulb replacement lamp building block units referred to as UVA blocks, with integrated power and controller and the integrated cooling mechanisms can be used. Cooling can be implemented with fans or heat exchangers or active cooling means or combinations of these components. Cooling can occur across or through the array. Building blocks may be square or round and may be stacked to build a complete tanning device, referred to as stacked block device.

In an example, a person with UV opaque protective eye-wear can be exposed to a tanning light and light therapy or a combination thereof in the presence of multiple types of light sources which includes a UVA LED array alone or in combination with the prior art UV light sources such as high pressure and low pressure fluorescent bulb within a tanning chamber. The chamber can optionally possess one or more UV opaque walls, a UV opaque tanning chamber door, a ventilation system, a cooling system, a safety switch connected to shut-off controller and/or system controller, a controller communication device, a high voltage ballast (for use with first embodiment of invention or fluorescent bulb and with low voltage LED power supply), and/or an external light output feedback sensor, for use with alternate low voltage embodiment of the present invention and calibration requirements.

Again, the chamber can be a booth or bed and can be enclosed or open. The chamber can be composed of a variety of materials including UV opaque film or UV opaque solid walls to control the exposure direction of the light. The LEDs can be directed to expose light within the chamber and can be on the same or on independent controls. In general, the internal surface of the chamber walls will be UV reflective while the external surface and the wall itself will be UV opaque.

For example, height dependent chambers with light saving feature sections of controllable UVA LEDs can selectively be turned off where the person in the tanning chamber does not require all of the controllable light sources (including UVA LEDs) turned on because of height, or because of the desire to tan (or not tan) specific parts of the body. For example, LEDs can be arranged and selectively powered to avoid tanning pre-cancer sites or moles. A LED controller may be present in the chamber (or outside the chamber) to adjust the height, pattern, brightness and other features of the tanning system. The controller has a manual controller input, an automatic height sensor input, or both. The controller can adjust brightness and duration of exposure based on the temperature of the devices with optional temperature sensor input. The controller can vary the pattern accordingly and indicate to the tanner the best direction to stand and in what position the extremities should be in order to have the best solution for obtaining the desired results if, for example, the chamber does not have a full 360 degrees of tanning. Alternatively, the height controller may be an external component to facilitate a full 360 degree of controllable UVA LED array. Additionally, one may include a master controller and master-slave communication device and slave-slave communication device. Tanning patterns may be recorded and used again to control or initiate a subsequent tanning session.

It is noted that personal slippers can improve health conditions on the surface of the device when shared, by reducing germ contamination between individuals. The personal slippers can be UV translucent or UV opaque depending on choice of person tanning.

Preferably, the person can be equipped with radio identification, UV opaque protective eye-wear (with an optional safety feature to indicate that the eyewear is worn) and user interface. The user communication and safety control system can be accessible from the inside and/or outside of the chamber containing receiver for UV opaque protective eye-wear with an identification device used to indicate the presence of the UV opaque protective eye wear within the chamber. The identification device may be wireless or a wired communication device.

FIG. 1 shows an electrical schematic diagram for powering the LEDs in the series connected LEDs (47) in the low voltage LED array (22) and metallic pins (10, 12) and external LED compatible power supply (20) responding to control from optional external light output feedback sensor (174) and house power connector (36). This embodiment utilizes a resistor (46) to limit the current to the series connected LEDs (47). The series connected LEDs (47) have multiple LEDs or a single LED depending on the voltage supplied and number LEDs per controlled power lines (49). If the design goals of further embodiments of the present invention requires a controllable power line for each LED then a single LED in the series connected LEDs (47) and LED (5) are identical. There is a tradeoff between providing control to each LED and the cost associated with the control circuits. Additionally, there is a tradeoff between cost of power supply and the failure of a single LED in an open failure mode to block the delivery of current to multiple LEDs in the series connected LEDs (47). LED compatible power supplies (20) designed for supplying current to individual LEDs is more expensive because the voltage conversion is wider and the current output is higher. The total current output from LED compatible power supply (20) is reduced by a factor calculated as the number of power lines (49) divided by the total number of LEDs in the further embodiment of invention (22). Therefore, depending upon the application and allowable failure modes, LEDs may have an arbitrary number of LEDs in series depending on the trade-off and application requirements. Also shown is a variable power supply which charges capacitors (45) in a selective manner.

Figure 2:
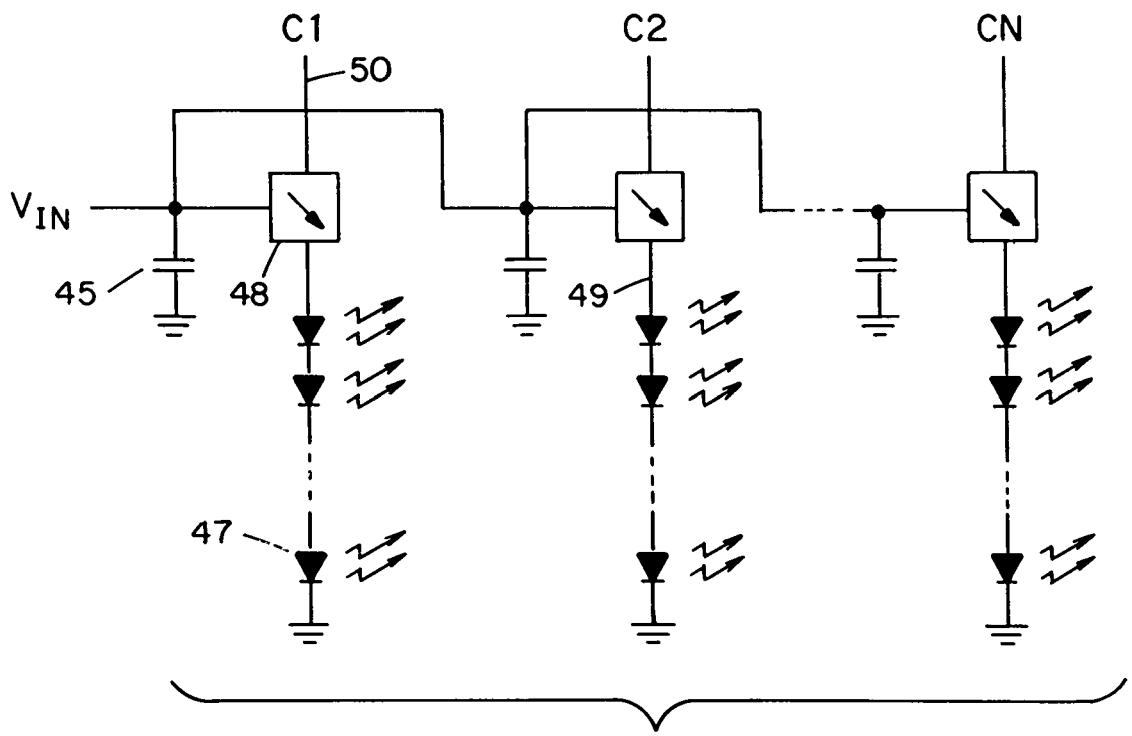
FIG. 2 shows an electrical schematic diagram of a LED power control circuit that utilizes a current control (48), and an optional capacitor (45). Current control (48) supplies current series connected LEDs (47) via controlled power line (49) power control line (50). Current control (48) may optionally vary the current delivered to series connected LEDs (47) over time as the encapsulation UV transmittance varies in order to calibrate the LEDs for a given usage history.

FIG. 2 shows an electrical schematic diagram of a LED power control circuit that utilizes a current control (48), and an optional capacitor (45). Current control (48) supplies current series connected LEDs (47) via controlled power line (49) power control line (50). Current control (48) may optionally vary the current delivered to series connected LEDs (47) over time as the encapsulation UV transmittance varies. Current control (48) may optionally vary the current delivered to series connected LEDs (47) over time to provide specific tanning patterns according to achieving arbitrary light therapy specific results.

Figure 3:
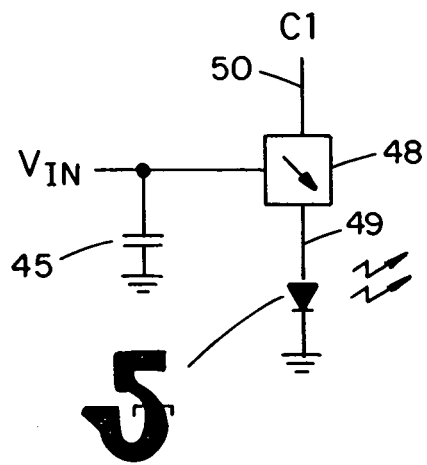
FIG. 3 shows an electrical schematic diagram of a LED power control circuit that utilizes a current control (48), and a capacitor (45), where current control (48) is attached to a single LED (5) connected to controlled power line (49) power control line (50).

FIG. 3 shows an electrical schematic diagram of a LED power control circuit that utilizes a current control (48), and a capacitor (45), where current control (48) is attached to a single LED (5) connected to controlled power line (49) power control line (50).

Figure 4:
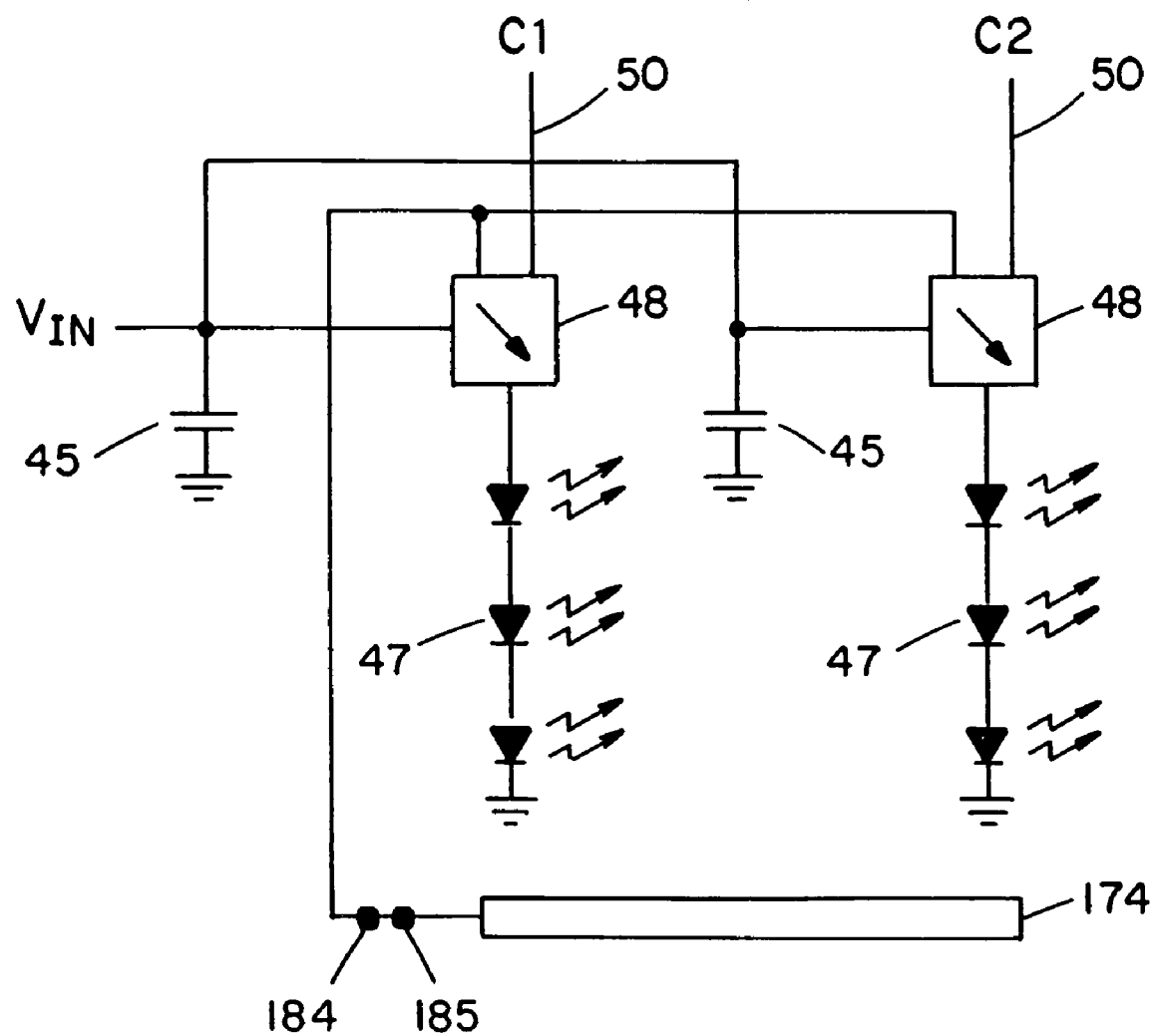
FIG. 4 shows an electrical schematic diagram of a LED power control circuit that utilizes said current controls (48), and an optional said capacitors (45). Said current controls (48) supplies current to said series connected LEDs (47) via said controlled power lines (49) responsive to said power control lines (50) and said external light output feedback sensor (174). The method of calibrating each separate said current controls by selectively turning on one said current control at a given time in order to measure the light output from the said series connected LEDs and calibrate each set of said series connected LEDs (47) separately. Current control (48) may optionally vary the current delivered to series connected LEDs (47) over time as the encapsulation UV transmittance varies. Also shown are permanently mounted connector (184) and portable connector (185) which allows said external light output feedback sensor (174) to be moved around within the tanning chamber and removed from the tanning chamber.

FIG. 4 shows an electrical schematic diagram of a LED power control circuit that utilizes said current controls (48), and an optional said capacitors (45). Said current controls (48) supplies current to said series connected LEDs (47) via said controlled power lines (49) responsive to said power control lines (50) and said external light output feedback sensor (174). The method of calibrating each separate said current controls by selectively turning on one said current control at a given time in order to measure the light output from the said series connected LEDs and calibrate each set of said series connected LEDs (47) separately. Current control (48) may optionally vary the current delivered to series connected LEDs (47) over time as the encapsulation UV transmittance varies. Also shown are optional permanently mounted connector (184) and portable connector (185) which allows said external light output feedback sensor (174) to be moved around within the tanning chamber and removed from the tanning chamber. The light output sensor may also be fixed inside the chamber or mounted to a translating and rotating mechanism to scan the chamber in a mechanical and automated manner.

The form factors for incorporating the LEDs can be optionally contoured to fit or conform to the body or body part of the individual user. For example, the form is a face tanning system incorporating LEDs and circuit board. The face tanning system is in the form of a face mask (optionally extending to the neck area or below), with optional ports for the eyes, nose and/or mouth and can incorporate one or more optional fans at the edge(s) of the mask for ventilation and cooling purposes, optional audio speakers for listening to music or environmental sounds with either stereo or quadraphonic audio input and/or microphone for verbal communications with optional telephonic capabilities, microphone input for further communications capability. Additionally, the mask can be characterized by an external LED compatible power supply with optional timer control, power switch, house power connector and/or external battery connector, an optional programming keypad for entering user codes and lockout features, key-lock, proximity switch to control the safety feature of closed to operate UV opaque shield with hinge attached to UV opaque face shield. A circuit board which has multiple current controls controlled by signals from control lines, and has connections to power lines, connections to UVA LEDs and connections to power source and current return drain on pins. In this embodiment, the pins can be flexible.

In another embodiment, the form encompasses the full head and neck tanning system. Again, as above, additional components can include audio speakers, external LED compatible power supply and house power connector. LEDs may be selectively powered to provide specific areas of tanning and may be turned off around the hair, which does not require exposure to UVA.

In yet another embodiment, a full or partial body tanning apparel can be made. Apparel can avoid golfer's tan by allowing full body exposure to the light while still providing privacy where the outer layer of the apparel is opaque. The apparel can be made of material that contains a UV blocking or reflecting component positioned to keep the UV light in the apparel. The apparel can be lined with a removable layer or a first inner layer can be a layer in between the outer and inner layer that contains the UVA LEDs and circuit board and the circuitry and cooling and controlling components. A UV translucent inner layer comes in contact with the client. For sanitary reasons the inner layer is preferably used exclusively by a single client and/or can be washed. This inner fabric will be completely or partially transparent to UV light. The inner fabric will also be able to diffuse the UV light in a manner that will allow the client to receive a consistent tan over the surface of the body. Controls selectively control the UVA LEDs to be energized in a desired pattern. This desired pattern may be saved and recalled automatically through the registration and control system connected to controlled power lines and a control line. A UV opaque zipper or other fastener can be used to get into the full body tanning apparel and limit the amount of UV radiation emitted. This embodiment of the invention will allow tanning slowly over a period of time preferably while sleeping. Slow tanning may be less stressful on the skin. Tanning apparel and sleeping bags may be used to slow down the tanning process, reduce the required light flux and can tan in a comfortable environment. Cooling systems can also be controlled by control system through control wires. External LED compatible power supplies and house power connectors can be incorporated into the device.

The apparel can have a layer of partially or fully UV opaque material, inside the inner layer of the full body tanning apparel next to the body covering parts of the client that require no UV exposure. Alternatively, the client can attach a patch to the skin to protect it from UV exposure. The use of partially or fully UV opaque filters results in a controlled tanning pattern without the need for granular control of the UVA LEDs.

Of course, multiple connections and controllers over various parts of the full body tanning apparel, can be used rather than a single controller or connector, whether the chamber is made of fabric, is flexible or rigid.

Modular selective tanning devices allow selectable patterns for tanning. Selective tanning is useful for eliminating or blending an uneven tan, such as a golfers tan, where parts of the body are over tanned and the goal is to obtain a less drastic change in skin color over a given area. Modular and selective tanning is also useful in medical cases such as a person with a medical skin condition that requires a prescribed light therapy as directed by a physician or other medical person or medical therapist.

Modular tanning apparel can be used as well. In this embodiment, the module connectors are connected to a common controller at the tanning apparel edge. An alternate design uses external connectors. Multiple two-dimensional components connected into three-dimensional assemblies are useful building block components for modular tanning apparel. Modular and selective tanning is useful in medical cases such as a person with a medical skin condition that requires a prescribed light therapy as directed by a physician or other medical person or medical therapist.

Various shapes of modular tanning apparels can be readily envisioned, including, for example, a torso, leg, foot, arm, pants, shirt. The shapes can be inter-connectable pieces of tanning apparel to build a complete or partial modular tanning suit. Arbitrary numbers of connector, arbitrary types of connectors, arbitrary shapes of components, and arbitrary materials of components, and arbitrary orientations of connectors allow for arbitrary tanning devices to be constructed.

A curved three-dimensional modular fabric component for completing power and control signal connections between tanning apparel components, with two sides having male style connector power pins and male style communications connector and two sides with female style hollow power connectors and female style communications connector. Alternatively, a curved three-dimensional modular fabric component with one, two or three sets of male connectors which would represent an end component or corner of the fabric can be made. Not shown is the curved three-dimensional modular fabric component with one, two or three sets of female connector which would represent an end component in the fabric.

Two-dimensional components used to build three-dimensional assemblies connections from one segment of clothing to another for power and control signals can be designed to keep electromagnetic interference to a minimum.

A three-dimensional modular fabric component, such as a rectangular component, for completing power and control signal connections between tanning apparel components, with two sides having male style connector power pins and male style communications connectors and two sides with female style hollow power connectors and female style communications connectors can be conveniently used. One or more of each component can be used. Not shown is one side with quartz or other UV translucent material to allow UV light to reach the skin. Arbitrary numbers of connector, arbitrary types of connectors, arbitrary shapes of components, and arbitrary materials of components, and arbitrary orientations of connectors allow for arbitrary tanning devices to be constructed.

Alternatively, a mechanical translating tanning system that has a spatial translating LED loop (or loops) that encircle(s) the tanner has the advantage of requiring fewer bulbs to tan the same area of skin over a longer period of time. This embodiment has a reduced cost because fewer UVA LEDs are required to produce the desired tan. Either the system (or loop) moves longitudinally with respect to the client, or the client may moves parallel with the axis of the loop, or both. The movement may be manual or it may be power assisted in a manual or automatic control manner. This system can accommodate a standing tanner or a prone tanner. The loop(s) can be mounted on a wall or ceiling-mounted track, for example, via a hinge to allow clients to enter and exit the chamber. The UV translucent bed may be acrylic. Translating LED loops may be comprised of combinations of controllable UVA LEDs to be selectively powered depending on position and area requiring tan.

Various wavelength LEDs can be used in combination and selectable and controlled for use in skin tanning and other light therapies as a multi-wavelength light bulb. For example, the UVA can be used in combination with yellow, orange, green, blue, red, violet, IR, fluorescent, and/or UVC, as modular or fixed designs, in combination or separate. Bulbs capable of producing various wavelengths can be combined in arbitrary patterns to, produce arbitrary light therapy devices. Further, the wavelength produced by any one LED can be varied. LEDs are produced by Cree, Inc. (Durham, N.C.), Nichia America Corp. (Mountville, Pa.) and Toyoda Gosei Ltd. (Japan).

The system can be used in conjunction with a payment system associated with, for example, a rental of tanning chamber, commercial sales and rental store and of the tanning systems as in indoor-tanning salons. Battery backup power supplies can be provided for operation of tanning equipment and control systems during momentary power outages. A computer based control and communications system for operating the tanning salon and associated controllable tanning equipment and personal services and communicating with other associated tanning salons and home offices via communications lines or via wireless communication system can be incorporated.

The use of multiple LEDs of various wavelength within a tanning chamber can also be used. Specifically useful for tanning are near-UV-blue LED, blue LED, blue-green LED, multi-bright LED, solid state laser light emitting device that radiates light capable of tanning or capable of providing light therapy of some benefit. Also envisioned is solid state nanostructure UV-laser chip for use in controlled multi-directional area specific tanning device optionally associated with camera for feed-forward control for determining exposure avoidance area and feedback control of specific light exposure areas. Alternatively, one may use tanning area specific mechanical translation device with laser chip based focused light source. Another embodiment includes focused light source utilizing LEDs on circuit board and translucent lens, optional translucent lens, and translucent lens to create a tightly focused light source which can be selectively powered depending on specific areas of skin to expose to light and in particular UVA light. Another embodiment includes focused light source utilizing any light source lens and translucent lens, optional UV translucent lens, and UV translucent lens to create a tightly focused UVA light source which can be selectively controlled by light controller depending on specific areas of skin to expose to light and in particular UVA light. Light controller may be a blocking type shutter or a deflecting mirror to effectively modulate the light emitting from focused light source.

In yet another embodiment, the wavelength of the LED can be controlled. For a given junction electric current and junction temperature, UVA LEDs generally emit photons around a peak wavelength in a narrow (approximately 10 nm) bell curve range of wavelengths. Differing LED types have differing peak wavelengths. UVA LEDs allow fine control for generating wavelengths. That is, the use of a plurality of the same or distinct LEDs can be used, optionally, in combination with multiple distinct operating conditions to independently control the emitted wavelengths. For example, a set of LEDs of a single LED type can be controlled with different junction currents and power duty cycles among the individual LEDs within the set of LEDs of a single LED type in order to broaden the spectral density of UV wavelengths emitted by the set as a whole. In addition, multiple sets of LEDs of differing types can be used to broaden the spectral density of UV wavelengths to a greater extent than is possible with a set of LEDs of a single type. The purpose of the manipulation of the LEDs is to be able to tailor the UV wavelength for a specific individual tanning session or specific light therapy requirements.

LEDs as a UV light source provide the capability of controlling the wavelengths produced. LEDs of varying types produce light at various wavelengths. By selectively controlling specific LEDs types within the light therapy device sequences of light can be applied at predetermined or arbitrary patterns with varying wavelengths. Examples of LED types include but are not limited to Cree (405-395 nm), Nichia (375), Toyoda Gosei, Marubeni America Corporation (364-380 nm), Crystal IS in collaboration with Palo Alto Research Center (355-365 nm). Additional LEDs that can be used in this device include organic light emitting devices.

Another method for controlling wavelength is based on varying the electrical current and/or junction temperature to the LEDs.

A single LED type at a given current and temperature will generally produce photons that have a wavelength distribution resembling a bell curve. Therefore, controlled current pulsing in combination of varying the duty-cycle of the LEDs power will control current and temperature conditions of the LED and results in wavelength shifts that will have additional light therapy benefits.

Generally, for a given UVA LED type, the shorter wavelengths, within the band of producible wavelengths, results from the lower junction currents.

An additional means to control the peak wavelength is varying the LED ambient cooling mechanism (e.g. fans, thermoelectric cooler, peltier effect cooling device, and compressor based air conditioners). A UVA LED assembly control system, comprising an analog or digital computer, a suitable algorithm, wavelength sensors, light intensity sensors, skin proximity sensors, and user interface for programming desired results, can be used to calculate the required variations to the current controllers and the duty cycle controllers and the ambient temperature controllers in order to produce a specific peak wavelength from a given set of UVA LEDs. The time of exposure for any given light therapy application may vary depending on the wavelength required and can be determined a-priori or in real time through such a control system.

LED type detecting sensors can be used to detect the types of LED that are present within the chamber. The use of such sensors may reduce the hazard of programming the control system for the wrong set of UV LED types. The detector can be mechanical in action with specific LED assemblies having specific cutouts for indicating type. The detector can be an RF ID system or other non-mechanical identification system. The detector can send various standardized controlled signals and power to the LED array to determine the capabilities of the LED assembly for use in the programming the control system.

A history of the use of the LED assembly can be stored on the LED assembly and read from the LED assembly in order to improve the effectiveness of the control system. Historical information can include one or more of the following: number of sessions, session type, duty cycles, electric current levels, power duty cycles, ambient temperatures, LED patterns and other LED type specific information. Information can also be stored in a remote location and a serialized coded key device (e.g. a memory chip, ROM, battery backed RAM, or optical memory) will provide the control system with a means of look-up for prior history of the LED assembly. The history of use of a particular LED assembly can be used in the control systems to calculate wavelength and exposure times for a desired light therapy session.

Additional sensors can be incorporated to further refine the control of the light therapy quality. For example, additional sensors could detect presence of particulate matter in the air which could affect wavelength and intensity levels.

A person in the upright or a person in the prone position can be exposed to a directionally controllable focused light source controlled either by controllable mirrors or controlled by tanning area specific mechanical translation device of focused light source or controlled by a combination of both methods to effectively tan only the desired areas. This allows blemished problem skin or pre-cancerous skin problem to remain unexposed to the focus light. In this manner a tan is blended into the skin whose surrounding skin becomes tanned as desired without damaging the problem skin.

Light emitting fabric can be rolled up to store and un-rolled to operate. A detection means for determining the state of the fabric, roll or un-rolled, for safe operation, referred to as roll-state-detector can be connected to external UV compatible power source to control application of power to flexible power pins. In the rolled up state the fabric LEDs are off. In the un-rolled state, the fabric is powered up or shut off manually when un-rolled. Additional components include a multi-purpose personal health device with display and power and communications connectors capable of performing multiple functions that may include but is not limited to detecting skin type, detecting person identification, detecting vitamin D production, and detecting other personal chemistry affected by light therapy and tanning light radiation.

One embodiment of a benefits communications means for advertising the advantages of the invention via print, or electronic, or audio means or any combination thereof in order to increase user awareness of the benefits of the present invention and all of its various embodiments which may include but is not limited to low voltage operation, low power operation, arbitrary patterns of area tanning, flexible or rigid form factors, no mercury, lighter and easier to move, lower safety costs, multiple form factors, clothing, tanning apparel and tunable wavelength given selectable multiple LEDs with various wavelengths.

Non-conducting housing for electrical connectors connecting power and control circuits between multiple modular LED replacement fluorescent bulb components and rotating power connectors can be used. External light output feedback sensor can be used to increase safety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A skin tanning chamber, the improvement comprising at least one light emitting diode emitting a UVA light, wherein the light emitting diode (LED) emits essentially only UVA light, and wherein the LED is incorporated into a rigid form.

2. The skin tanning chamber of claim 1 wherein the chamber is a bed or booth.

3. The skin tanning chamber of claim 1 further comprising at least one LED emitting a UVB and/or a UVC light.

4. The skin tanning chamber of claim 3 wherein the LED emitting the UVA light is under independent control from the LED emitting UVC light.

5. The skin tanning chamber of claim 1 the improvement comprising a plurality of LEDs emitting UVA light.

6. The skin tanning chamber of claim 5 further comprising a means for controlling the electric current to each LED to maintain a constant total radiant flux over the life time of each LED.

7. The skin tanning chamber of claim 5 further comprising a means for controlling the LEDs to allow radiation to selected portions of the skin.

8. The skin tanning chamber of claim 5 further comprising a means for controlling the period of exposure.

9. The skin tanning chamber of claim 8 further comprising a means for storing records of use.

10. The skin tanning chamber of claim 1 wherein the LED is incorporated into a form which is adapted to fit into a standard fluorescent bulb fixture.

11. The skin tanning chamber of claim 10 wherein the form farther comprises an internal power converter.

12. The skin tanning chamber of claim 1 wherein the LEDs are ventilated.

13. The skin tanning chamber of claim 12 wherein the LEDs are ventilated by a fan directing air longitudinally across the LEDs.

14. The skin tanning chamber of claim 13 wherein the LEDs are disposed within a transparent tube characterized by one or more perforations which provide for air flow out of the tube.

15. The skin tanning chamber of claim 14 wherein the tube is characterized by a closed end and an open end, wherein the air is directed through the open end and out the perforations.

16. The skin tanning chamber of claim 15 wherein the density of perforations on the distal end of the tube, with respect to the open end, is greater than the density of perforations on the proximal end.

17. The skin tanning chamber of claim 15 wherein the perforations on the distal end of the tube, with respect to the open end, are larger than the perforations on the proximal end.

18. The skin tanning chamber of claim 15 comprising a bed and a circuit board characterized by an array of UVA LEDs.

19. The skin tanning chamber of claim 18 wherein the circuit board is selected from the group consisting of (a) rigid, (b) curved, and (c) flexible.

* * * * *